US012565676B2

(12) United States Patent
    Kotseroglou et al.

(10) Patent No.:    US 12,565,676 B2
(45) Date of Patent:       Mar. 3, 2026

(54) SYSTEMS AND METHODS FOR SEPARATING DECODED ARRAYS

(71) Applicant: REVERE BIOSENSORS, LLC, Birmingham, MI (US)

(72) Inventors: Theofilos Kotseroglou, Birmingham, MI (US); Vladimir Bashkirov, Birmingham, MI (US); Robert Charles Kain, Birmingham, MI (US)

(73) Assignee: Revere BioSensors, LLC, Worcester, MA (US)

( * ) Notice: Subject to any disclaimer, the term of this patent is extended or adjusted under 35 U.S.C. 154(b) by 864 days.

(21) Appl. No.: 17/435,204

(22) PCT Filed: Feb. 28, 2020

(86) PCT No.: PCT/US2020/020355
    § 371 (c)(1),
    (2) Date: Aug. 31, 2021

(87) PCT Pub. No.: WO2020/180670
    PCT Pub. Date: Sep. 10, 2020

(65) Prior Publication Data
    US 2022/0136043 A1     May 5, 2022

Related U.S. Application Data

(60) Provisional application No. 62/846,483, filed on May 10, 2019, provisional application No. 62/812,740, filed on Mar. 1, 2019.

(51) Int. Cl.
    *C12Q 1/6837*      (2018.01)
    *B01L 3/00*        (2006.01)
    *C12Q 1/6869*      (2018.01)

(52) U.S. Cl.
    CPC ...... *C12Q 1/6837* (2013.01); *B01L 3/502707* (2013.01); *C12Q 1/6869* (2013.01);
    (Continued)

(58) Field of Classification Search
    None
    See application file for complete search history.

(56) References Cited

U.S. PATENT DOCUMENTS

| | | |
|---|---|---|
| 5,376,252 A | 12/1994 | Ekstroem et al. |
| 5,510,270 A | 4/1996 | Fodor et al. |
| | (Continued) | |

FOREIGN PATENT DOCUMENTS

| | | |
|---|---|---|
| CN | 101087890 A | 12/2007 |
| CN | 101090979 A | 12/2007 |
| | (Continued) | |

OTHER PUBLICATIONS

U.S. Appl. No. 15/776,244 Notice of Allowance dated Mar. 21, 2023.

(Continued)

*Primary Examiner* — Brian R Gordon
(74) *Attorney, Agent, or Firm* — Wilson Sonsini Goodrich & Rosati

(57) ABSTRACT

Methods and compositions for the fabrication and use of arrays are disclosed. Methods of the disclosure include separating decoded arrays, such as bead arrays, into independent sections and subsections. Methods of the disclosure can enable more economical fabrication of arrays suitable for conducting various assays, such as detection of target analytes in a sample.

17 Claims, 7 Drawing Sheets

(52) U.S. Cl.
CPC .................. *B01L 2200/0668* (2013.01); *B01L 2300/0636* (2013.01); *B01L 2300/0819* (2013.01)

(56) References Cited

U.S. PATENT DOCUMENTS

| | | | |
|---|---|---|---|
| 5,563,034 A | 10/1996 | Brink et al. | |
| 5,593,867 A | 1/1997 | Walker et al. | |
| 6,004,752 A * | 12/1999 | Loewy | C07H 21/00 435/6.19 |
| 6,225,077 B1 * | 5/2001 | Schmidt | C12Q 1/6837 435/6.12 |
| 6,506,564 B1 * | 1/2003 | Mirkin | C12Q 1/6839 435/6.12 |
| 6,812,334 B1 * | 11/2004 | Mirkin | C12Q 1/6818 435/6.12 |
| 6,821,770 B1 | 11/2004 | Hogan | |
| 7,083,917 B2 | 8/2006 | Barany et al. | |
| 7,349,158 B2 * | 3/2008 | Moon | B01L 3/502761 359/569 |
| 7,399,643 B2 * | 7/2008 | Moon | B01L 3/5085 436/501 |
| 7,566,533 B2 * | 7/2009 | Jacobs | G01N 33/6845 435/7.1 |
| 8,105,471 B1 | 1/2012 | Han et al. | |
| 9,683,960 B2 | 6/2017 | Bercovici et al. | |
| 11,725,233 B2 | 8/2023 | Kain et al. | |
| 11,939,638 B2 | 3/2024 | Kain et al. | |
| 2001/0016361 A1 * | 8/2001 | Seul | H05H 3/04 435/287.2 |
| 2001/0055760 A1 | 12/2001 | Chenchik | |
| 2002/0015952 A1 * | 2/2002 | Anderson | B01J 19/0046 435/287.2 |
| 2002/0081714 A1 * | 6/2002 | Jain | B03C 1/035 436/526 |
| 2002/0137031 A1 | 9/2002 | Wolber | |
| 2003/0044855 A1 * | 3/2003 | Anderson | G01N 33/54313 435/7.9 |
| 2003/0104434 A1 * | 6/2003 | Fan | C12Q 1/6858 435/6.12 |
| 2003/0228697 A1 * | 12/2003 | Kocher | B01L 3/545 506/41 |
| 2004/0171053 A1 * | 9/2004 | Hu | B82Y 30/00 435/7.1 |
| 2004/0202577 A1 | 10/2004 | Mcneil et al. | |
| 2004/0219530 A1 | 11/2004 | Brousseau et al. | |
| 2005/0032095 A1 | 2/2005 | Wigler et al. | |
| 2005/0079517 A1 * | 4/2005 | Goncharko | B01L 3/50853 435/6.12 |
| 2005/0089889 A1 | 4/2005 | Ramsing et al. | |
| 2005/0136395 A1 | 6/2005 | Mittmann et al. | |
| 2005/0170362 A1 | 8/2005 | Wada et al. | |
| 2005/0255459 A1 | 11/2005 | Fofanov et al. | |
| 2006/0194215 A1 * | 8/2006 | Kronick | B01L 3/5027 435/6.11 |
| 2006/0194223 A1 | 8/2006 | Andreoli et al. | |
| 2006/0228256 A1 * | 10/2006 | McDevitt | G01N 21/05 422/82.05 |
| 2006/0228716 A1 | 10/2006 | Nobile et al. | |
| 2006/0240416 A1 * | 10/2006 | Banerjee | G01N 33/54346 435/7.1 |
| 2007/0053800 A1 * | 3/2007 | Lehto | B01L 3/502715 422/400 |
| 2007/0077645 A1 * | 4/2007 | Aoyagi | G01N 35/1065 435/287.2 |
| 2007/0087362 A1 | 4/2007 | Church et al. | |
| 2007/0166741 A1 * | 7/2007 | Heil | C12Q 1/6837 435/7.1 |
| 2007/0178516 A1 | 8/2007 | Sosnowski et al. | |
| 2007/0207060 A1 * | 9/2007 | Zou | G01N 21/6452 422/68.1 |
| 2008/0057513 A1 | 3/2008 | Farrell | |
| 2008/0194424 A1 * | 8/2008 | Kim | B82Y 30/00 506/16 |
| 2008/0260577 A1 * | 10/2008 | Shirai | G01N 21/01 422/52 |
| 2009/0047673 A1 * | 2/2009 | Cary | C12Q 1/6837 73/61.71 |
| 2009/0117573 A1 | 5/2009 | Fu et al. | |
| 2009/0181378 A1 | 7/2009 | Sanders et al. | |
| 2010/0201381 A1 * | 8/2010 | Iqbal | B01L 3/502715 430/311 |
| 2010/0240544 A1 * | 9/2010 | Liu | C12Q 1/6837 506/17 |
| 2011/0105356 A1 * | 5/2011 | DeRosier | B01J 19/0046 506/13 |
| 2011/0136699 A1 * | 6/2011 | Shirazi | B01L 3/50855 29/829 |
| 2012/0122737 A1 | 5/2012 | Sabot et al. | |
| 2015/0099673 A1 * | 4/2015 | Fodor | C12N 15/1065 506/37 |
| 2015/0126378 A1 | 5/2015 | Rothberg et al. | |
| 2015/0284786 A1 | 10/2015 | Shapero et al. | |
| 2016/0177382 A1 | 6/2016 | Han et al. | |
| 2016/0253584 A1 * | 9/2016 | Fodor | C12Q 1/6813 235/494 |
| 2016/0289669 A1 * | 10/2016 | Fan | B01L 3/502761 |
| 2018/0245142 A1 * | 8/2018 | So | C12Q 1/6816 |
| 2018/0265918 A1 | 9/2018 | Shirai et al. | |
| 2019/0039069 A1 | 2/2019 | Marshall et al. | |
| 2019/0076847 A1 * | 3/2019 | Donovan | G01N 15/1484 |
| 2020/0087717 A1 | 3/2020 | Kain et al. | |
| 2020/0172985 A1 * | 6/2020 | Kain | C12Q 1/701 |
| 2021/0262019 A1 * | 8/2021 | Alvarado Martinez | C12Q 1/6837 |
| 2021/0370296 A1 * | 12/2021 | Handique | C12Q 1/6806 |
| 2022/0136043 A1 | 5/2022 | Kotseroglou et al. | |
| 2023/0203579 A1 * | 6/2023 | Glezer | C12Q 1/6837 435/6.11 |
| 2024/0218431 A1 | 7/2024 | Kain et al. | |
| 2025/0027139 A1 * | 1/2025 | Ramsey | C12Q 1/686 |

FOREIGN PATENT DOCUMENTS

| | | |
|---|---|---|
| CN | 101157952 A | 4/2008 |
| CN | 104419764 A | 3/2015 |
| CN | 104677972 A | 6/2015 |
| CN | 104897758 A | 9/2015 |
| CN | 108474028 A | 8/2018 |
| EP | 3280820 A1 | 2/2018 |
| JP | 2001514906 A | 9/2001 |
| JP | 2005509127 A | 4/2005 |
| WO | WO-0242775 A2 | 5/2002 |
| WO | WO-02101094 A1 | 12/2002 |
| WO | WO-2004092733 A1 | 10/2004 |
| WO | WO-2007027495 A1 | 3/2007 |
| WO | WO-2014185803 A2 | 11/2014 |
| WO | WO-2015079446 A1 | 6/2015 |
| WO | WO-2016138496 A1 | 9/2016 |
| WO | WO-2016160844 A2 | 10/2016 |
| WO | WO-2016187234 A1 | 11/2016 |
| WO | WO-2017087416 A1 | 5/2017 |
| WO | WO-2017132630 A1 | 8/2017 |
| WO | WO-2017205827 A1 | 11/2017 |
| WO | WO-2018208804 A1 | 11/2018 |
| WO | WO-2020180670 A1 | 9/2020 |

OTHER PUBLICATIONS

U.S. Appl. No. 16/612,339 Office Action dated Jun. 27, 2022.
U.S. Appl. No. 16/612,339 Office Action dated Mar. 16, 2023.
Co-pending U.S. Appl. No. 18/336,201, inventors Kain; Robert Charles et al., filed Jun. 16, 2023.
U.S. Appl. No. 15/776,244 Notice of Allowance dated Apr. 5, 2023.
U.S. Appl. No. 16/612,339 Notice of Allowance dated Sep. 20, 2023.
PCT/US2016/062090 Invitation to Pay Additional Fees dated Jan. 11, 2017.

(56)　　　　　References Cited

OTHER PUBLICATIONS

U.S. Appl. No. 16/612,339 Notice of Allowance dated Feb. 15, 2024.

Bates et al. Cooperativity of paired oligonucleotide probes for microarray hybridization assays. Anal Biochem. Jul. 1, 2005;342(1):59-68. doi: 10.1016/j.ab.2005.03.030. Epub Apr. 15, 2005.

Deyholos et al., High-density microarrays for gene expression analysis. Cytometry. 43(4):229-238 (2001).

EP18798644.3 Extended European Search Report dated Nov. 13, 2020.

European Patent Application No. 16866968.7 Supplementary Search Report dated Jun. 7, 2019.

International Application No. PCT/US16/62090 International Preliminary Report on Patentability Mailed May 31, 2018, pp. 1-14.

International Application No. PCT/US2016/062090 International Search Report and Written Opinion Mailed Mar. 17, 2017, pp. 1-15.

Miller et al., Basic concepts of microarrays and potential applications in clinical microbiology. Clinical Microbiology Review. 22(4):611-633 (2009).

Molecular Devices: "Genepix 4000B Microarray Scanner: User Guide". Retrieved from the Internet URL: http://mdc.custhelp.comjeufjassetsjcontentjGenePix_4000B_UserGuide.pdf (2010).

PCT/US2018/031636 International Preliminary Report on Patentability dated Nov. 12, 2019.

PCT/US2018/031636 International Search Report and Written Opinion dated Jul. 11, 2018.

PCT/US2020/020355 International Search Report and Written Opinion dated Jul. 15, 2020.

U.S. Appl. No. 15/776,244 Final Office Action dated Jun. 4, 2021.

U.S. Appl. No. 16/612,339 Final Office Action dated Aug. 25, 2021.

U.S. Appl. No. 16/612,339 Final Office Action dated Feb. 8, 2021.

U.S. Appl. No. 15/776,244 Office Action dated Oct. 2, 2020.

Vilensky et al. Oxidized Porous Silicon Nanostructures Enabling Electrokinetic Transport for Enhanced DNA Detection. Advanced Functional Materials, vol. 25, Issue 43, pp. 6725-6732 (Nov. 18, 2015). First published Oct. 6, 2015. DOI: https://doi.org/10.1002/adfm.201502859.

Woo et al., A comparison of cDNA, oligonucleotide, and Affymetrix GeneChip gene expression microarray platforms. Journal of Biomolecular Techniques. 15(4):276-284 (2004).

Divne et al. A DNA microarray system for forensic SNP analysis. Forensic Science International 154 (2005) 111-121. Available online Dec. 2, 2004.

EP20767191.8 Extended European Search Report dated Oct. 18, 2022.

Huang et al. Efficient SNP Discovery by Combining Microarray and Lab-on-a-Chip Data for Animal Breeding and Selection. Microarrays 2015, 4, 570-595.

Kim et al. Three-dimensional microstructures fabricated by multi-step electrochemical etching of aluminum sheet. Transducers 2009, Denver, CO, USA, Jun. 21-25, 2009, pp. 1059-1062.

Komura, et al. Genome-wide detection of human copy number variations using high-density DNA oligonucleotide arrays. Genome Res. 2006; 16(12): 1575-84.

Li et al. Multiplexed analysis of polymorphisms in the HLA gene complex using bead array chips. Tissue Antigens 2004: 63:518-528 (2004).

U.S. Appl. No. 15/776,244 Office Action dated Jun. 13, 2022.

* cited by examiner

SYSTEMS AND METHODS FOR SEPARATING DECODED ARRAYS

CROSS-REFERENCE

This application claims the benefit of U.S. Provisional Application No. 62/812,740, filed Mar. 1, 2019 and U.S. Provisional Application No. 62/846,483, filed May 10, 2019, which applications are incorporated herein by reference in their entireties.

BACKGROUND

Currently, random assembly-based detection systems involve the loading of bead sensors on to a substrate where the beads can self-assemble in wells. The position of the beads is then identified or "decoded" by going through a series of assay and imaging steps to decode the identities of the thousands to millions of unique bead types using few cycles via combinatorial decoding.

Multiple independent sample sections (e.g., sections where single samples can be assayed) can be included on a single substrate in order to reduce the costs associated with the substrate, the manual handling of the part (e.g., as it is moved from an assay step to an imaging step), and the reagent volumes used in the decoding process.

The physical size, dimensions, and total number of sample sections on a specified substrate is limited by sample separation gasketing technology. In order to separately address sample sections with different physical samples, a gasket is implemented to create a physical barrier such that samples do not comingle and cause one sample to pollute another sample.

SUMMARY

Disclosed herein are methods, compositions and systems related to the design, fabrication, and use of arrays including separating decoded arrays, such as bead arrays, into independent sections and subsections.

Disclosed herein are methods of creating an array, comprising: a) obtaining an array substrate comprising a plurality of independent sections, wherein each independent section comprises a plurality of array sites, wherein identities of probes at the plurality of array sites have been identified; and b) separating the plurality of independent sections from each other such that the identities of probes at the plurality of array sites in a given independent section remain identified.

In some aspects the array substrate comprises a bead array substrate and wherein the plurality of array sites comprise beads in wells. In some aspects the plurality of array sites comprise array spots. In some aspects the identities of the probes at the array sites have been identified through a decoding process. In some aspects the identities of the probes at the plurality of array sites in a given independent section remain identified by using fiducials. In some aspects the identities of the probes at the plurality of array sites in a given independent section remain identified by labeling at least some of the plurality of array sites. In some aspects the labeling comprises labeling array sites that do not contain probes. In some aspects the identities of the probes at the plurality of array sites in a given independent section remain identified by parsing a decoding file into sub-files for each independent section. In some aspects the probes comprise oligonucleotides. In some aspects the probes comprise proteins. In some aspects the probes comprise antibodies. In some aspects the separating comprises dicing the array substrate. In some aspects the separating comprises etching the array substrate. In some aspects the separating comprises cutting the array substrate. In some aspects an independent section of the plurality of independent sections comprises fewer than 10,000,000 array sites. In some aspects an independent section of the plurality of independent sections comprises fewer than 1,000,000 array sites. In some aspects an independent section of the plurality of independent sections comprises fewer than 500,000 array sites. In some aspects an independent section of the plurality of independent sections comprises fewer than 100,000 array sites. In some aspects an independent section of the plurality of independent sections comprises fewer than 10,000 probes per array site. In some aspects an independent section of the plurality of independent sections comprises fewer than 5,000 probes per array site. In some aspects an independent section of the plurality of independent sections comprises fewer than 1,000 probes per array site. In some aspects an array site of the plurality of array sites comprises fewer than 10,000 probes. In some aspects an array site of the plurality of array sites comprises fewer than 5,000 probes. In some aspects an array site of the plurality of array sites comprises fewer than 1,000 probes. In some aspects the plurality of independent sections are spaced apart on the array substrate by buffer zones of less than or equal to about 50 micrometers (μm).

Disclosed herein are compositions, comprising: an array substrate comprising an array of wells organized in a plurality of independent sections, wherein the independent sections are spaced apart from each other by less than or equal to 50 micrometers (μm).

In some aspects an independent section of the plurality of independent sections comprises fewer than 10,000,000 wells. In some aspects an independent section of the plurality of independent sections comprises fewer than 1,000, 000 wells. In some aspects an independent section of the plurality of independent sections comprises fewer than 500, 000 wells. In some aspects an independent section of the plurality of independent sections comprises fewer than 100, 000 wells. In some aspects the wells comprise beads, and wherein the beads comprise probes. In some aspects the beads comprise fewer than 10,000 probes per bead. In some aspects the beads comprise fewer than 5,000 probes per bead 5,000. In some aspects the beads comprise fewer than 1,000 probes per bead.

Disclosed herein are compositions, comprising one or more of the following elements: an array substrate comprising an array of wells, wherein the array of wells is fluidically addressable individually from any other array of wells, and wherein the array of wells comprises fewer than 10,000,000 wells. In some aspects the array of wells comprises fewer than 1,000,000 wells. In some aspects the array of wells comprises fewer than 500,000 wells. In some aspects the array of wells comprises fewer than 100,000 wells. In some aspects the wells comprise beads, and wherein the beads comprise probes. In some aspects the beads comprise fewer than 10,000 probes per bead. In some aspects the beads comprise fewer than 5,000 probes per bead 5,000. In some aspects the beads comprise fewer than 1,000 probes per bead.

DETAILED DESCRIPTION

Introduction

Figure 1A:
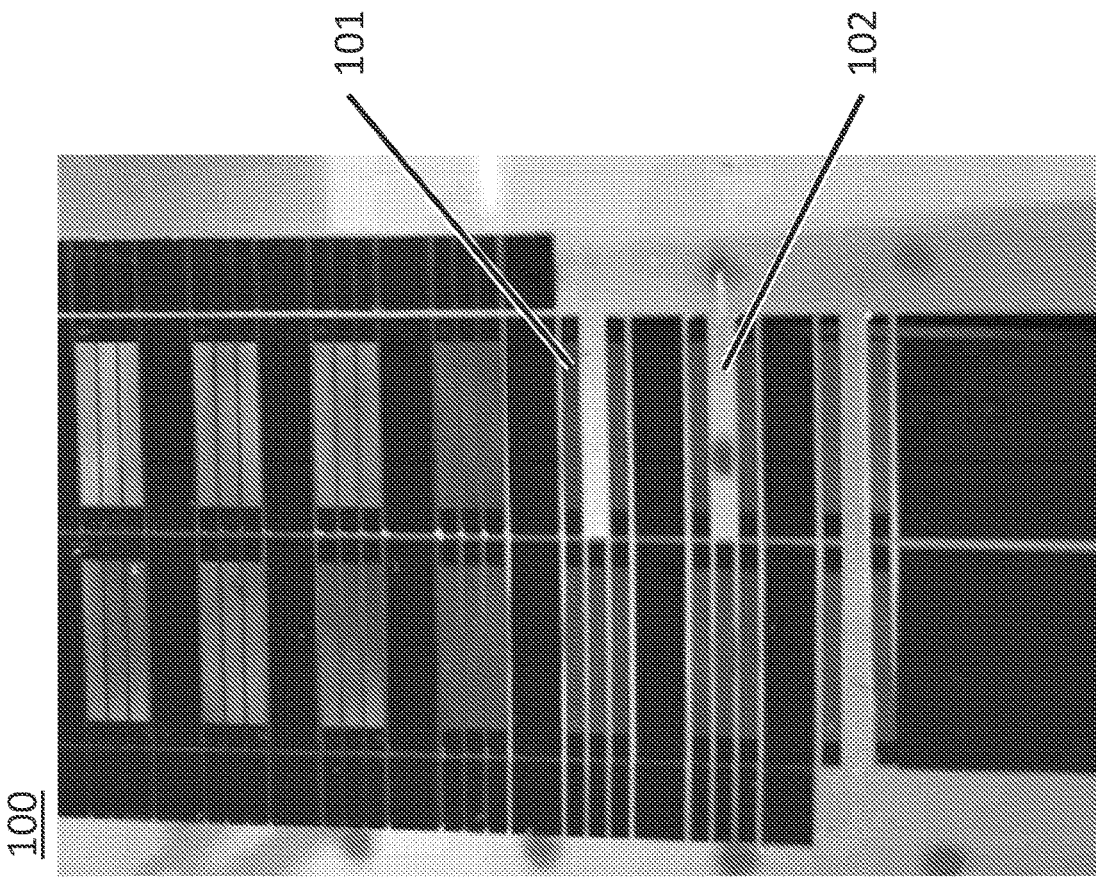
FIG. 1A shows an exemplary bead array substrate diced into independent sample sections.

Currently, random assembly-based detection systems involve the loading of bead sensors on to a substrate where the beads can self-assemble in wells. The position of the beads is then identified or "decoded" by going through a series of assay and imaging steps to decode the identities of the thousands to millions of unique bead types using few cycles via combinatorial decoding.

Multiple independent sample sections (e.g., sections where single samples can be assayed) can be included on a single substrate in order to reduce the costs associated with the substrate, the manual handling of the part (e.g., as it is moved from an assay step to an imaging step), and the reagent volumes used in the decoding process. The buffer zone or spacing between sample sections can be less than or equal to about 100 micrometers (m), 90 μm, 80 μm, 70 μm, 60 μm, 50 μm, 40 μm, 30 μm, 20 μm, or 10 μm. For existing approaches, the number of sample sections can be constrained by the physical design of sample separation gaskets.

Individual sample sections on a bead array can be further divided into decoding subsections in order to help with registration of individual beads within a single decoding section. These subsections can be separated by buffer zones where it is not possible for beads to self-assemble (e.g., no wells are present, surface coatings discourage bead aggregation). These separation zones can assist in the registrations (e.g., optical registration) of randomly assembled beads within the subsections. In an example, these subsections can be square in geometry and separated by buffer zones of approximately 30 μm. In other cases, the buffer zone or spacing between subsections can be less than or equal to about 100 μm, 90 μm, 80 μm, 70 μm, 60 μm, 50 μm, 40 μm, 30 μm, 20 μm, or 10 μm. The cost of a single sample section is therefore the cost to produce a decoded substrate divided by the number of sample sections on the substrate.

The present disclosure describes separating the individual sample sections into separate components (sometimes called "chiplets"), while maintaining sufficient information to enable the use of the decode library information generated during the decoding process, and not reducing the performance of the beads in an assay.

The present disclosure further describes separating sample sections into multiple independent components, or decoding subsections, each capable of assaying the sample and therefore becoming independently addressed with a sample. Along with physically separating the sample sections into decoding subsections, the decode library information can be parsed into separate files while maintaining geometric positioning information relating to sample subsections. Bead registration information can also be maintained through fiducials or other geometric "mile markers" on the substrate.

This separation of subsample sections, transforming the subsections into independent sample sections, eliminates the limitations imposed by the design of physical sample separation gaskets. This approach can enable the cost of individual sample sections to further be reduced by the number of these sample subsections separated from a single original sample section. These exponential reductions in cost along with the ability to use the sample sections singularly vs in a multiplexed manner will enable new applications for low cost single use testing, such as in point of care infectious disease testing.

The present disclosure describes combining multiple unique and novel processes together, such as separating the substrates physically (e.g., dicing the substrates), without harming the individual bead sensors or changing the substrate surface characteristics, and while maintaining the positioning information of individual sample sections after separation, and parsing the decode library file (e.g., algorithmically) to enable the bead sensors in the multiple independent sample sections to be decoded.

Substrate Separation

Substrates (e.g., bead arrays) can be separated into sections or subsections by a variety of methods. A substrate can be diced, etched, laser cut (e.g., stealth diced), diced before grinding (e.g., partially diced then wafer thinned), or separated by other means. The substrate can be protected prior to separation, for example by a film, coating, or other physical barrier. For example, prior to dicing, a substrate can be mounted on dicing tape. Substrate protection can be used to reduce or prevent contamination or destruction of substrate features, such as bead array wells or loaded beads.

Decoding Subsections

A decode file for a bead array can be parsed into separate files, for example corresponding to individual sample sections or decoding subsections. Registration information for each section or subsection can be identified in a decode file, and single decode file can be reformatted or parsed into multiple decode files each corresponding to the sections or subsections of the bead array.

A substrate can include one or more markers, such as fiducials or "mile markers", to assist in maintaining bead registration information. Markers can comprise physical markers, including but not limited to numbers, letters, geometric shapes, and combinations thereof, in the substrate (e.g., etched, printed, or otherwise visibly marked on the substrate). Markers can comprise changes in the shape of a section or subsection. Bead registration information can also be maintained by use of image recognition algorithms, for example aligning a section or subsection based on which beads are positive under certain assay conditions (e.g., with certain labels). In some cases, a correctly aligned section or subsection would exhibit all beads of a given type responding (e.g., emitting light) under a certain assay, while an incorrectly aligned section or subsection may show some or many bead types responding without all beads of a given bead type responding. Markers can include features designed specifically for use as fiducials or mile markers, or markers can be features included on the substrate for other purposes which can also be used as fiducials or mile markers. Markers can be located around the edges of the array, within the interior of the array, or both.

Beads

Beads in bead arrays of the present disclosure can be loaded with fewer targets per bead than conventional bead arrays. In some cases, beads can comprise fewer than or equal to 10,000 targets per bead, 1000 targets per bead, 100 targets per bead, 50 targets per bead, 20 targets per bead, or 10 targets per bead (e.g., in average number of targets per bead on the array).

Bead arrays of the present disclosure can comprise fewer beads than conventional bead arrays, such as bead arrays in commercial use. In some cases, bead arrays can comprise no more than 10,000,000 beads, 5,000,000 beads, 2,000,000 beads, 1,000,000 beads, 500,000 beads, 200,000 beads, 100,000 beads, 50,000 beads, 20,000 beads, 10,000 beads, 5,000 beads, 2,000 beads, or 1,000 beads, less than 1,000 beads, or any number spanned by the range defined thereby.

Reducing the number of targets per bead while keeping large numbers of beads (e.g., billions) can result in dilution of sample analytes over the beads. However, reducing the number of targets per bead while also reducing the number of beads (e.g., millions or thousands) can enhance signal to noise ratio (SNR). Thus, smaller arrays (e.g., independent sample sections or subsections) can allow the analysis of smaller sample volumes without dilution of sample analyte among the probes.

Accordingly, disclosed herein are systems, compositions and methods related to improved SNR upon analysis of a dilute sample. Some such methods comprise one or more of the steps of providing a sample at a concentration below a level for sufficient SNR measurement, such as of a sequencing reaction, providing a reduced number of annealing sites, such as a reduced number relative to commercially available systems, methods or kits, hybridizing the sample to the beads and obtaining a signal from the chip. Through the disclosure herein, the sample is concentrated at the reduced number of annealing sites, such that the signal at these sites is stronger or more focused, or both stronger and more focused, so as to increase a signal, increase an SNR or both increase a signal and increase a SNR.

Providing a reduced number of target annealing sites variously comprises providing fewer beads, providing a reduced surface area such as by separating an array into independent sections or otherwise as disclosed herein, providing fewer oligonucleotides per bead, or combinations of more than one of the immediately previously mentioned options. That is, some approaches comprise contacting a dilute sample or a sample having nucleic acids below a threshold expected for success in sequencing, imaging or otherwise gathering data, to a reduced number of beads, having a reduced per bead annealing site number, in a reduced area. As a consequence of such a reduction, one observes in some cases an increased signal, increased SNR, or both an increased signal and an increased SNR. Often, such an increase results from concentrating the sample at the reduced number of sites at a reduced area, such that local signal is strengthened relative to comparable reactions such as those recommended or commercially used.

Beads can also be used as fiducials or mile markers as discussed herein. For example, beads without targets can be used to fill wells on a bead array which would otherwise be empty; the location of such "empty" beads can be used as can be used as fiducials or mile markers. In some examples, "empty" beads are loaded using nucleic acids of known source, often a source distinct from that of a sample to be assayed. Any readily available nucleic acid source is suitable for such a loading, such as E. coli nucleic acids, salmon nucleic acids or material, bovine material or bovine targets, or chicken material or chicken targets, for example. Other sources are also suitable. Many such materials are suitable, provided that they are readily distinguished from sample nucleic acids if the assay requires them to be. In some cases, tags (e.g., fluorescent markers) can be attached to the material on "empty" beads for use as fiducials. In other cases, "empty" beads can be loaded with tags (e.g., fluorescent markers, tracer DNA which can be labeled) for use as fiducials. Employing "empty" beads as fiducials can be used as part of an array decoding process and/or to track the registration of a decoded array during a substrate separation process.

Applications

After separation and decode parsing, sections or subsections can be used for a variety of applications. Sections or subsections can be contacted with a sample, with or without the use of a sample handling device. Sections or subsections can be fluidically addressable independent of any other sections or subsections; for example, a section or subsection can be placed in an individual microfluidic channel to allow a sample to be contacted to it without being contacted to any other section or subsection. Probes on a section or subsection can be used to determine the presence or absence of given analytes in a sample (e.g., by hybridization or other binding). Results from a section or subsection assay can be read out optically (e.g., with fluorescent markers), such as by using the parsed decode file corresponding to the section or subsection to decode the identity of given beads on the section or subsection.

Probe sets and probe layouts can be designed for a range of different applications. For example, probes can be selected and arranged as described in PCT/US2016/062090 filed 2016 Nov. 15 (published as WO2017087416A1 on 2017 May 26) or in PCT/US2018/031636 filed 2018 May 8 (published as WO2018208804A1 on 2018 Nov. 15), each of which is hereby incorporated by reference in its entirety.

Multiple Target Arrays

The present disclosure also provides methods, compositions, and systems for arrays with multiple targets. These arrays can be fabricated by a variety of methods, including but not limited to spotted arrays, synthesized arrays, bead arrays, and the separated decoded array sections and subsections of the present disclosure.

An array can comprise probes that target more than one category or source of genetic feature. For example, an array can comprise one or more sets of probes that target genetic features informative of pathogens in a subject and one or more sets of probes that target genetic features informative of the subject itself (e.g., subject genotype). Categories of genetic features can include genetic features associated with a subject (e.g., a human, a mammal, a bird, another animal, a plant), with microorganisms associated with a subject (e.g., microbiome, infectious agents, or others), and microorganisms associated with an environment (e.g., soil or water microbiome).

Different categories of genetic feature may have different optimal sample preparations. Nonetheless, when a sample is prepared for analysis on an array comprising probes that target more than one category of genetic feature, it may be prepared in a way that is not optimal for one or more of the categories of genetic feature. Optimal sample preparations may differ in their preferred buffers, nucleic acid concentrations, processing temperatures, processing times, enzymes, membranes, or other parameters. When processing such a sample for analysis, the parameters may each independently be chosen to optimize one category, the other category, or neither (e.g., a compromise value). While this may result in less than optimal sample processing, it allows one sample to be processed and analyzed together for multiple categories of genetic features. For example, extracted DNA for human samples may be optimally diluted to one concentration (e.g., 5 ng/uL) while extracted DNA for microorganisms in stool may be optimally diluted to a different concentration (e.g., 2.5 ng/uL); a sample being analyzed for genetic features of both human and microorganism origin may be diluted to the optimal concentration for one category, the other category, or a compromise between the two.

Definitions

The below terms are discussed to illustrate meanings of the terms as used in this specification, in addition to the understanding of these terms by those of skill in the art. As used in the specification and claims, the singular forms "a", "an" and "the" can include plural references unless the context clearly dictates otherwise. For example, the term "a cell" can include a plurality of cells, including mixtures thereof.

As used herein, the term "epigenome" refers to changes to genetic material, or the protein expression of genetic material, that are not reflected at the sequence level such as DNA methylation and chromatin restructuring or remodeling. The "transcriptome" refers to the entirety of gene transcripts (mRNA) synthesized by an organism under certain environmental conditions. A transcriptome data set includes, without limitation, qualitative and quantitative information as to the activation or deactivation of expression of a gene of interest. Transcriptome also includes RNA transcripts that do not code for proteins (non-coding RNA or ncRNA) including microRNAs, piwiRNA, structural RNAs, RNA that binds to proteins, telomerase RNA, and transposon RNA. The "exome" refers to the part of the genome formed by exons, the sequences which, when transcribed, remain within the mature RNA. "Microbiome" refers to the entirety of the genomes within a biological sample, regardless of the species, usually microbial in origin.

As used herein, the term "genetic feature" refers to any genome, genotype, haplotype, chromatin, chromosome, chromosome locus, chromosomal material, deoxyribonucleic acid (DNA), allele, gene, gene cluster, gene locus, genetic polymorphism, genetic mutation, genetic mutation rate, nucleotide, nucleotide base pair, single nucleotide polymorphism (SNP), restriction fragment length polymorphism (RFLP), variable tandem repeat (VTR), copy number variant (CNV), microsatellite sequence, genetic marker, sequence marker, sequence tagged site (STS), plasmid, transcription unit, transcription product, gene expression level, genetic expression (e.g., transcription) state, ribonucleic acid (RNA), complementary DNA (cDNA), conserved region, and pathogenicity island, including the nucleotide sequence and encoded amino acid sequence associated with any of the above. Genetic features can be determinative of, indicative of, implicated in, associated with, or correlated with various traits, including but not limited to resistance or susceptibility to a drug, drug tolerance, drug intolerance, virulence or pathogenicity, and disease state or disease susceptibility. An epigenetic feature is any feature of genetic material—all genomic, vector and plasmid DNA and chromatin—that affects gene expression in a manner that is heritable during somatic cell divisions and sometimes heritable in germline transmission, but that is non-mutational to the DNA sequence and is therefore fundamentally reversible, including but not limited to methylation of DNA nucleotides and acetylation of chromatin-associated histone proteins. As used herein, therefore, genetic sequence data can include, without limitation, nucleotide sequences, deoxyribonucleic acid (DNA) sequences, and ribonucleic acid (RNA) sequences.

The term "subject-specific feature" as used herein can refer to any feature or attribute that is capable of distinguishing one subject from another. Subject-specific features can distinguish between subjects at the level of an individual subject, a sub-species, a strain, a species, a genus, a family, an order, a class, a phylum, a kingdom, or a domain. In some cases, a subject-specific feature is a genetic feature. The genetic feature, as described above, can be present on a nucleic acid isolated from a subject. In some cases, a subject-specific feature can relate to a feature or features that distinguish a set of functions. This could be accomplished, for example, by designing probes to target a single gene, a plurality of genes, or genomic regions with known epigenomic functions such as promoter regions. A subject-specific feature can be represented as a probe on a detection device. The probes representing the subject-specific feature can be capable of binding to one or more target nucleic acid sequences obtained from a subject. In some cases, the subject-specific feature comprises a plurality of non-identical probes, each capable of distinguishing a subject from another. In some cases, a specific subject, such as a strain of a microbe, can be distinguished by one or multiple features on a detection device, including features that are unique to the target strain, unique to the species containing the strain, contained in conserved regions that exist in the strain, or that recognize pathogenicity islands contained within the strain. In some cases, it can be valuable to identify simply pathogenicity islands, as this can indicate that a subject requires more testing.

The term "assembly" can be any computational process in which sequence strings produced by a sequencer or mass spectrometer are merged between one another with the objective to reconstruct at least a larger portion of a starting or original sequence string, from which at least some of, up to the set of all sequence strings were derived. In some instances, an assembly is from an individual organism. In some instances, multiple individuals are can be used to create an assembly. In some instances, an assembly is created de novo, without the use of a reference sequence. In some instances, an assembly is created using a reference sequence. The reference sequence can be a genome from the same species. The reference genome can be a genome from a closely related species.

The term "subject", as used herein, generally refers to a specific source of genetic materials. The subject can be a biological entity. The biological entity can be a plant, animal, pathogen, or microorganism, including, e.g., bacteria, viruses, fungi, and protozoa. The subject can be an organ, tissue, or cell. A subject can be obtained in vivo or cultured in vitro. The subject can be a cell line. The subject can be propagated in culture. The subject can be disease cells. The subject can be cancer cells. The subject can be a bird. The subject can be a mammal. The mammal can be a human. The subject can mean an individual representation of the specific source of genetic material (e.g. the subject can be a particular individual human or a particular bacterial strain). Alternatively, the subject can be a general representation of a kind of specific source of genetic materials, e.g. the subject can be any and all members of a single species. The subject can also be a portion of a genome, for example if the sample does not contain a full genome. Alternate subjects include reverse-transcribed cDNA library material or other material indicative of transcriptome levels, nucleic acids obtained from circulating free sources, such as nucleic acids circulating in blood or present in other source. Such nucleic acids are often not uniformly from a single organismal source, but are nonetheless 'subjects. Similarly, in some cases samples comprise synthetically synthesized nucleic acids rather than or in addition to nucleic acids from an organismal source. Generally, any material potentially comprising nucleic acids is a suitable subject in some cases.

The term "pooled" as used herein can refer to grouping together or mixing of non-identical probes prior to hybridization to a sample. The non-identical probes can be part of the same set of probes. Alternatively, the probes from two or more sets of probes can be pooled. Pooled probes can be mixed in equal or unequal amounts.

A "sample" or "nucleic acid sample" can refer to any substance containing or presumed to contain nucleic acid. The sample can be a biological sample obtained from a subject. The nucleic acids can be RNA, DNA, e.g., genomic DNA, mitochondrial DNA, viral DNA, synthetic DNA, or cDNA reverse transcribed from RNA. The nucleic acids in a nucleic acid sample can serve as templates for extension of a hybridized primer. In some cases, the biological sample is a liquid sample. The liquid sample can be, for example, whole blood, plasma, serum, ascites, semen, cerebrospinal fluid, sweat, urine, tears, saliva, buccal sample, cavity rinse, or organ rinse. The liquid sample can be an essentially cell-free liquid sample (e.g., plasma, serum, sweat, urine, tears, etc.). In other cases, the biological sample is a solid biological sample, e.g., feces, hair, nail, or tissue biopsy, e.g., a tumor biopsy. A sample can also comprise in vitro cell culture constituents (including but not limited to conditioned medium resulting from the growth of cells in cell culture medium, recombinant cells and cell components). A sample can comprise or be derived from cancer cells. A sample can comprise a microbiome.

A "complex sample" as used herein refers to a sample that includes two or more subjects or that includes material (e.g., nucleic acids) from two or more subjects. A complex sample can comprise genetic material from two or more subjects. A complex sample can comprise nucleic acid molecules from two or more subjects. A complex sample can comprise nucleic acids from two or more strains of bacteria, viruses, fungi and the like. A complex sample can comprise two or more resolvable subjects (i.e., two or more subjects that are distinguishable from one another). In some cases, complex samples can be obtained from the environment. For example, a complex sample can be an air sample, a soil or dirt sample or a water sample (e.g., river, lake, ocean, wastewater, etc.). Environmental samples can comprise one or more species of bacteria, viruses, protozoans, algae, fungi and the like. A complex sample can comprise cell free DNA.

"Nucleotides" can be biological molecules that can form nucleic acids. Nucleotides can have moieties that contain not only the known purine and pyrimidine bases, but also other heterocyclic bases that have been modified. Such modifications include methylated purines or pyrimidines, acylated purines or pyrimidines, alkylated riboses, or other heterocycles. In addition, the term "nucleotide" includes those moieties that contain hapten, biotin, or fluorescent labels and can contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the like.

"Nucleotides" can also include locked nucleic acids (LNA) or bridged nucleic acids (BNA). BNA and LNA generally refer to modified ribonucleotides wherein the ribose moiety is modified with a bridge connecting the 2' oxygen and 4' carbon. Generally, the bridge "locks" the ribose in the 3'-endo (North) conformation, which is often found in the A-form duplexes. The term "locked nucleic acid" (LNA) generally refers to a class of BNAs, where the ribose ring is "locked" with a methylene bridge connecting the 2'-O atom with the 4'-C atom. LNA nucleosides containing the six common nucleobases (T, C, G, A, U and mC) that appear in DNA and RNA are able to form base-pairs with their complementary nucleosides according to the standard Watson-Crick base pairing rules. Accordingly, BNA and LNA nucleotides can be mixed with DNA or RNA bases in an oligonucleotide whenever desired. The locked ribose conformation enhances base stacking and backbone pre-organization. Base stacking and backbone pre-organization can give rise to an increased thermal stability (e.g., increased Tm) and discriminative power of duplexes. LNA can discriminate single base mismatches under conditions not possible with other nucleic acids.

The terms "polynucleotides", "nucleic acid", "nucleotides" and "oligonucleotides" can be used interchangeably. They can refer to a polymeric form of nucleotides of any length, either deoxyribonucleotides or ribonucleotides, or analogs thereof. Polynucleotides can have any three-dimensional structure, and can perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component.

A "variant" can be an alteration in the normal sequence of a nucleic acid sequence (e.g., a gene), or any sequence that differs from a reference, such as a consensus, for example a consensus previously generated or concurrently generated. Variants may differ in sequence at a single base, a plurality of bases, or through presence of an insertion or deletion relative to a reference. In some instances, a genotype and corresponding phenotype is associated with a variant. In other instances, there is no known function of a variant. A variant can be a SNP. A variant can be a SNV. A variant can be an insertion of a plurality of nucleotides. A variant can be a deletion of a plurality of nucleotides. A variant can be a mutation. A variant can be a copy number variation. A variant can be a structural variant. A variant can be a nucleic acid deviation between two or more individuals in a population.

The term "target polynucleotide" or "target nucleic acid" as used herein, generally refers to a polynucleotide of interest under study. In certain cases, a target polynucleotide contains one or more sequences that are of interest and under study. A target polynucleotide can comprise, for example, a genomic sequence. The target polynucleotide can comprise a target sequence whose presence, amount, and/or nucleotide sequence, or changes in these, are desired to be determined. A target polynucleotide can comprise non-coding regions of a genome. A target nucleotide can comprise any nucleic acid present in or expected to be present in a subject or in a sample.

The term "genome" can refer to the genetic complement of a biological organism, and the terms "genomic data" and "genomic data set" include sequence information of chromosomes, genes, or DNA of the biological organism.

The term "genomic data," as used herein, refers to data that can be one or more of the following: the genome or exome sequence of one or more, or any combination or mixture of one or more, mitochondria, cells, including eggs and sperm, tissues, neoplasms, tumors, organs, organisms, microorganisms, viruses, individuals, or cell free DNA, and further including, but not limited to, nucleic acid sequence information, genotype information, gene expression information, genetic data, epigenetic information including DNA methylation, acetylation or similar DNA modification data, RNA transcription, splicing, editing or processing information, or medical, health or phenotypic data, or nutritional, dietary or environmental condition or exposure information or other attribute data of any microorganism, virus, cell, tissue, neoplasm, tumor, organ, organ system, cell-free sample (e.g. serum or media), individual or group of samples or individuals. Accordingly, the term "genomic sequence," as used herein, refers to a sequence that occurs in a genome. Because RNAs are transcribed from a genome, this term encompasses sequence that exist in the nuclear genome of an organism, as well as sequences that are present in a cDNA copy of an RNA (e.g., an mRNA) transcribed from such a genome. "Genomic sequence" can also be a sequence that occurs on the cytoplasm or in the mitochondria.

The terms "determining," "measuring," "evaluating," "assessing," "assaying," and "analyzing" can be used interchangeably herein to refer to any form of measurement, and can include determining if an element is present or not as well as making a quantitative assessment as to amount of a molecule. These terms can include both quantitative and/or qualitative determinations. Assessing can be relative or absolute. "Assessing the presence of" can include determining the amount of something present, as well as determining whether it is present or absent.

The term "genomic fragment", as used herein, can refer to a region of a genome, e.g., an animal or plant genome such as the genome of a eukaryote, prokaryote such as an archaea or eubacteria, or a virus, such as *E. coli*, human, monkey, rat, fish or insect or plant, or of any organism mentioned elsewhere herein or known in the art, or known or expected by one of the art to have nucleic acids. A genomic fragment may or may not be adaptor ligated. A genomic fragment can be adaptor ligated (in which case it has an adaptor ligated to one or both ends of the fragment, to at least the 5' end of a molecule), or non-adaptor ligated.

The term "barcode" as used herein, generally refers to a sequence of nucleotides that can encode information about an assay. In some instances, barcodes are unique. A barcode sequence can encode information relating to the identity of an interrogated allele, identity of a target polynucleotide or genomic locus, identity of a sample, a subject, or any combination thereof. A barcode sequence can be a portion of a primer, a reporter probe, or both. A barcode sequence can be at the 5'-end or 3'-end of an oligonucleotide, or can be located in any region of the oligonucleotide. Barcode sequences can be non-naturally occurring, e.g. sequences which do not occur in the sample under study. In other instances, naturally occurring sequences can be used as barcodes or as a part of a barcode sequence. In some instances, junctions, where nucleic acids have been joined can serve as bar codes. In some instances, sequencing adaptors can serve as barcodes or as a part of barcodes. In some instances, the barcodes are in excess of a target molecule, e.g. a genomic sequence of interest. In some instances, a barcode is associated with a target molecule randomly or semi-randomly. In some instances, a barcode is associated with a target molecule by design.

The term "mutation", as used herein, generally refers to a change of the nucleotide sequence of a genome relative to a reference. Mutations often result in genomic variants. Mutations can involve large sections of DNA (e.g., copy number variation). Mutations can involve whole chromosomes (e.g., aneuploidy). Mutations can involve small sections of DNA. Examples of mutations involving small sections of DNA include, e.g., point mutations or single nucleotide polymorphisms, multiple nucleotide polymorphisms, insertions (e.g., insertion of one or more nucleotides at a locus), multiple nucleotide changes, deletions (e.g., deletion of one or more nucleotides at a locus), and inversions (e.g., reversal of a sequence of one or more nucleotides).

The term "locus", as used herein, can refer to a location of a gene, nucleotide, or sequence on a chromosome. An "allele" of a locus, as used herein, can refer to an alternative form of a nucleotide or sequence at the locus. A "wild-type allele" generally refers to an allele that has the highest frequency in a population of subjects. A "wild-type" allele generally is not associated with a disease. A "mutant allele" generally refers to an allele that has a lower frequency that a "wild-type allele" and can be associated with a disease. A "mutant allele" may not have to be associated with a disease. The term "interrogated allele" generally refers to the allele that an assay is designed to detect.

The term "single nucleotide polymorphism", or "SNP", as used herein, generally refers to a type of genomic sequence variation resulting from a single nucleotide substitution within a sequence. "SNP alleles" or "alleles of a SNP" generally refer to alternative forms of the SNP at particular locus. The term "interrogated SNP allele" generally refers to the SNP allele that an assay is designed to detect.

EXAMPLES

Example 1—Separating a Bead Array into Independent Sample Sections

Figure 1B:
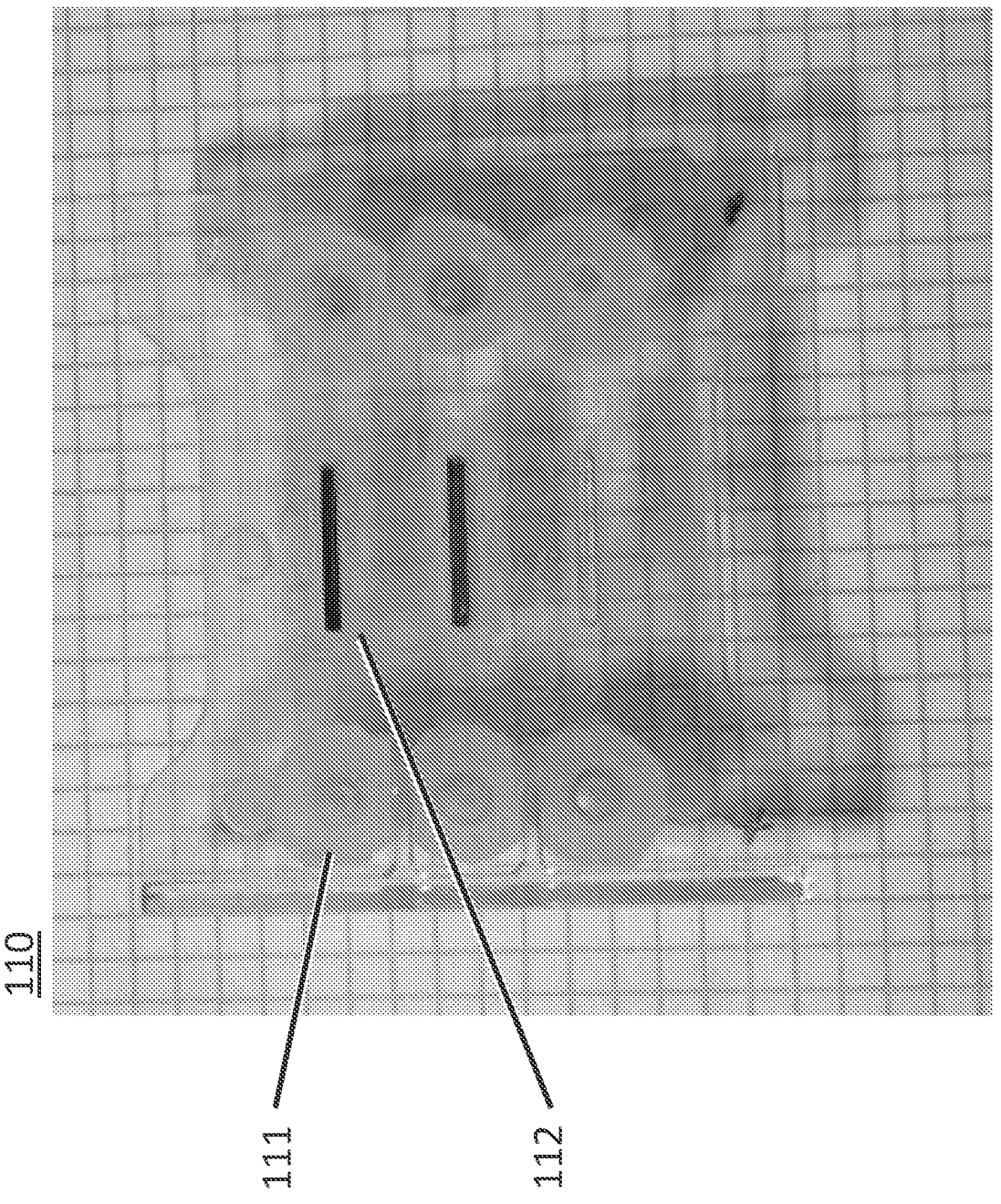
FIG. 1B shows diced independent sample sections loaded into flow cells.

An array substrate comprising multiple independent sample sections was separated by dicing so that each independent sample section can be individually addressed and used for sample analysis. FIG. 1A shows a bead array 100 (Illumina) that has been diced into 72 sections 101, each of which is an independent sample section ("chiplet"). FIG. 1B shows a microfluidic device 110 with microfluidic channels 111 into which chiplets 112 have been loaded, each chiplet in its own separate channel. Each chiplet comprises approximately 490,000 beads. Edges and fiducial markers of the bead array are retained, allowing parsing and tracking of the original bead array decoding information without need for more involved imaging registration or pattern recognition approaches.

The bead array can be diced into more sections. For example, each independent sample section in the bead array in FIG. 1A can be diced into two subsections, yielding 144 chiplets from one original bead array. In this approach, edges and fiducial markers are still retained, and so parsing and tracking of the original bead array decoding information is still achievable without need for more involved imaging registration or pattern recognition approaches.

Example 2—Contacting Independent Sample Sections with Sample

Figure 2A:
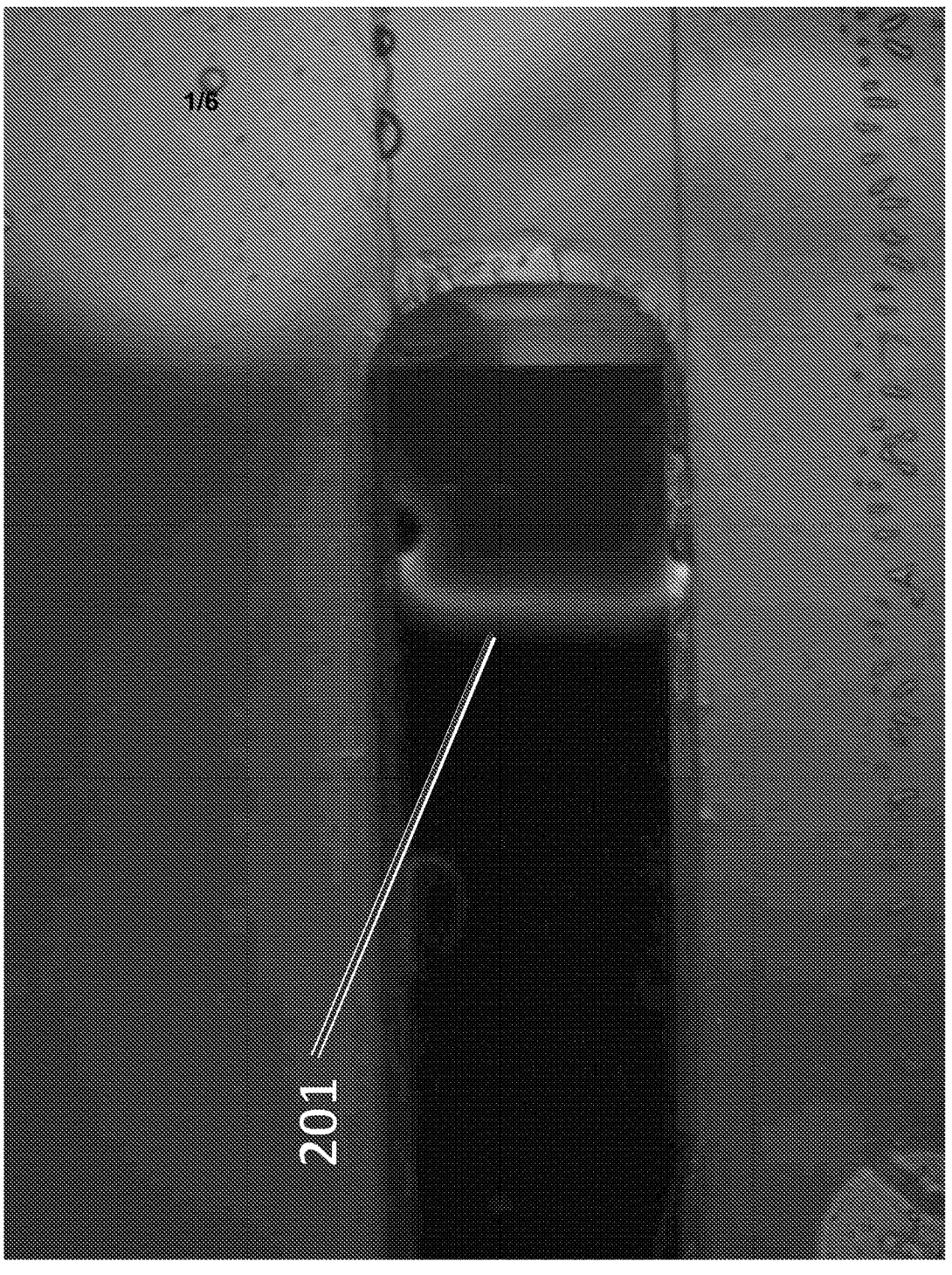
FIG. 2A shows a sample loaded onto a diced independent sample section using isotachophoresis (ITP).
Figure 2B:
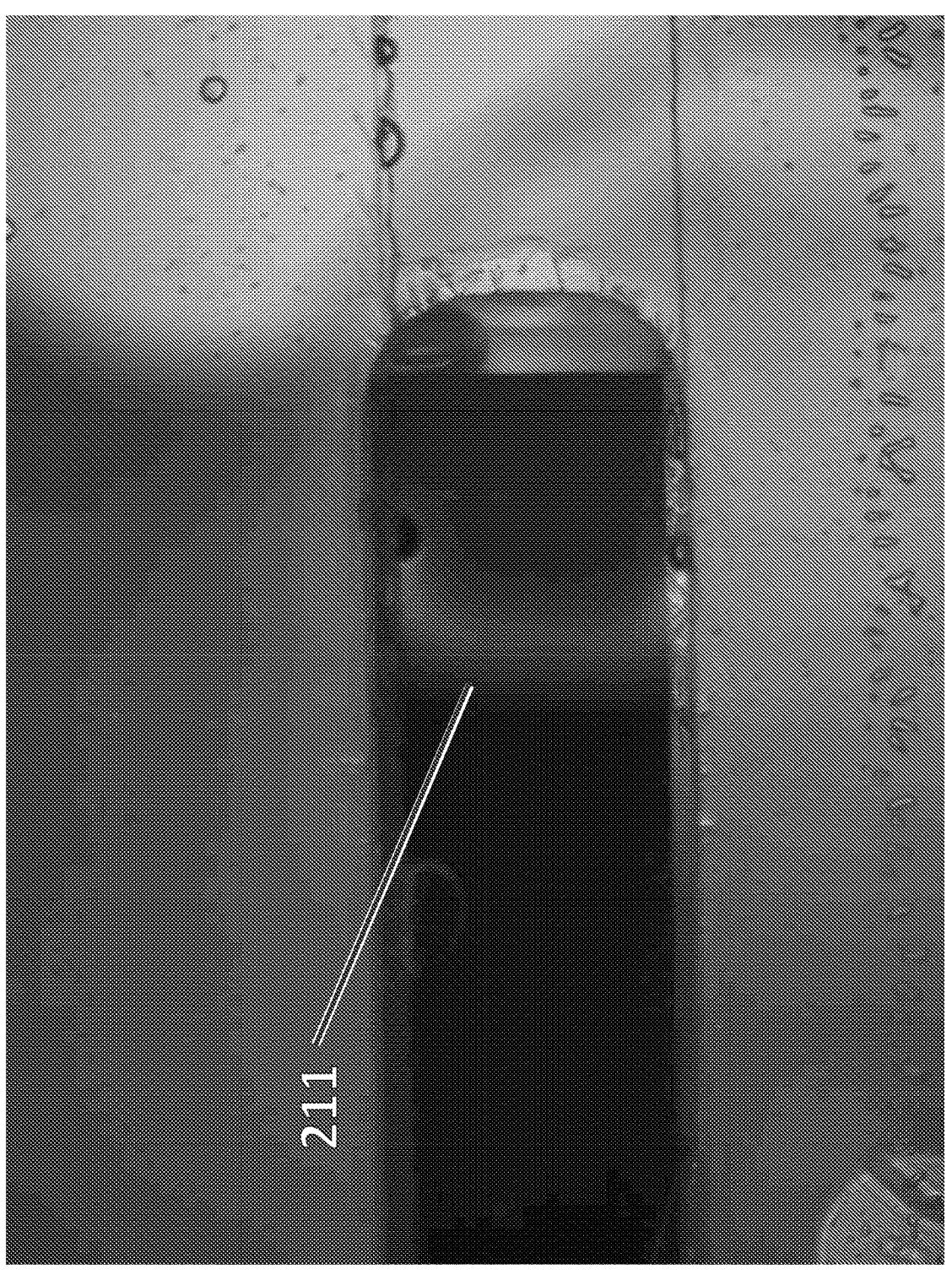
FIG. 2B shows a sample contacted with a diced independent sample section at time=0 minutes.
Figure 2C:
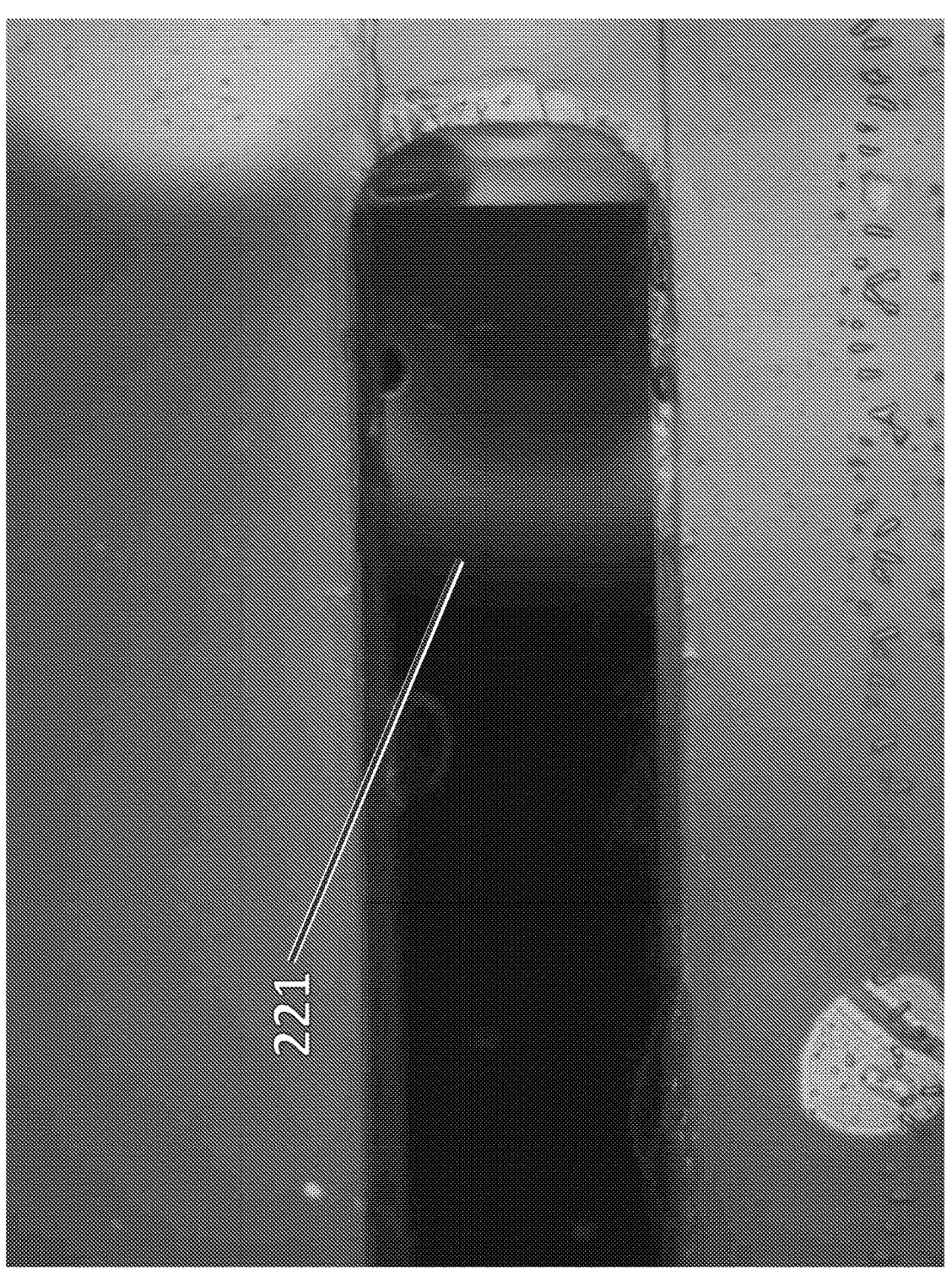
FIG. 2C shows a sample contacted with a diced independent sample section at time=2 minutes.
Figure 2D:
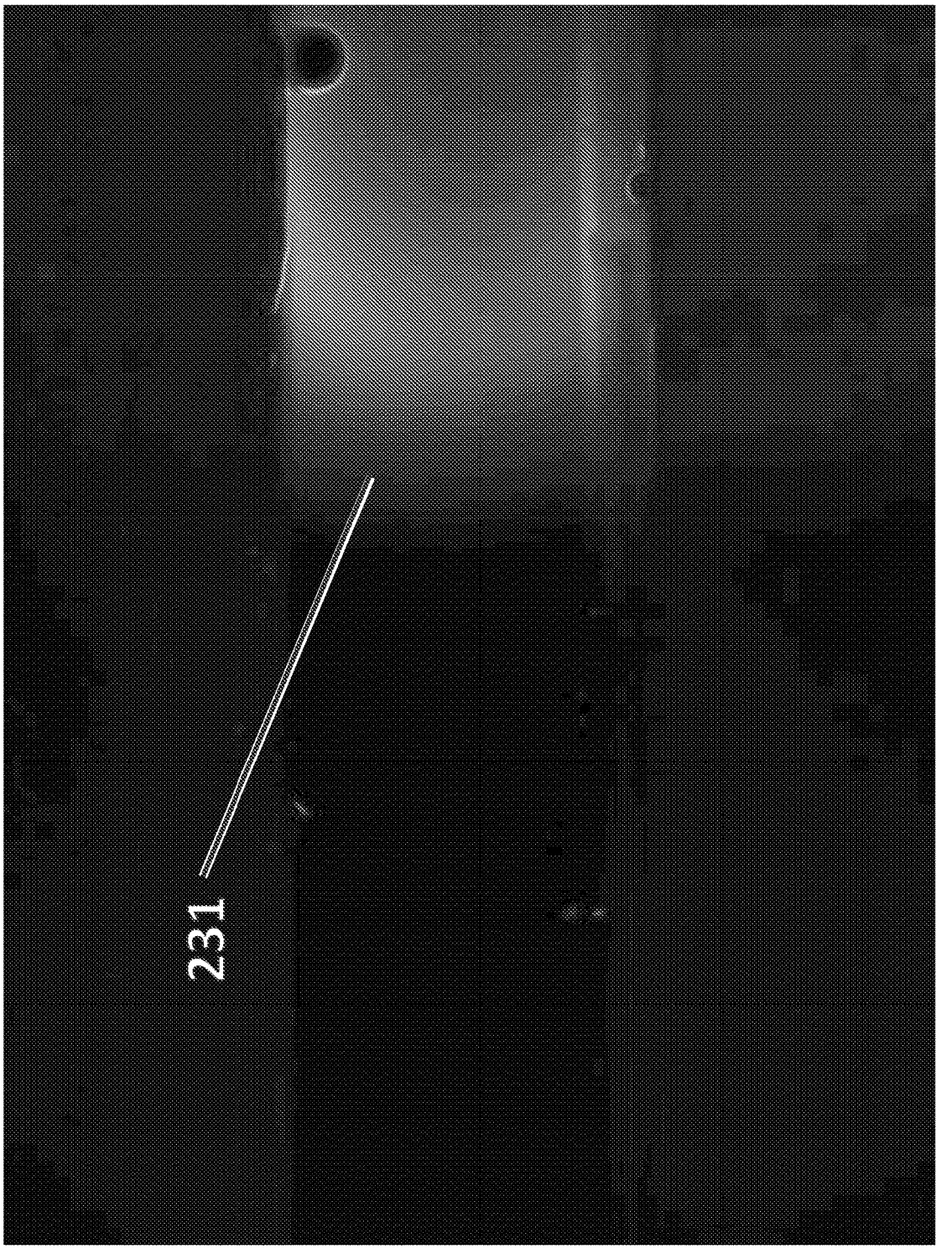
FIG. 2D shows a sample contacted with a diced independent sample section at time=6 minutes.

Independent sample sections were diced apart from an array substrate and placed into separate microfluidic flow cell channels (for example, as shown in Example 1). FIG. 2A shows a band of sample nucleic acids 201 with concentration 0.1 nM of target being loaded onto an independent sample section in a microfluidic channel using isotachopho-resis (ITP) at time t=−5 seconds before the sample is allowed to diffuse over the independent sample section. FIG. 2B shows the sample band 211 at time t=0 minutes of diffusion. FIG. 2C shows the sample band 221 at time t=2 minutes of diffusion. FIG. 2D shows the sample band 231 at time t=6 minutes of diffusion.

Example 3—Sample Analysis Workflow

Figure 3:
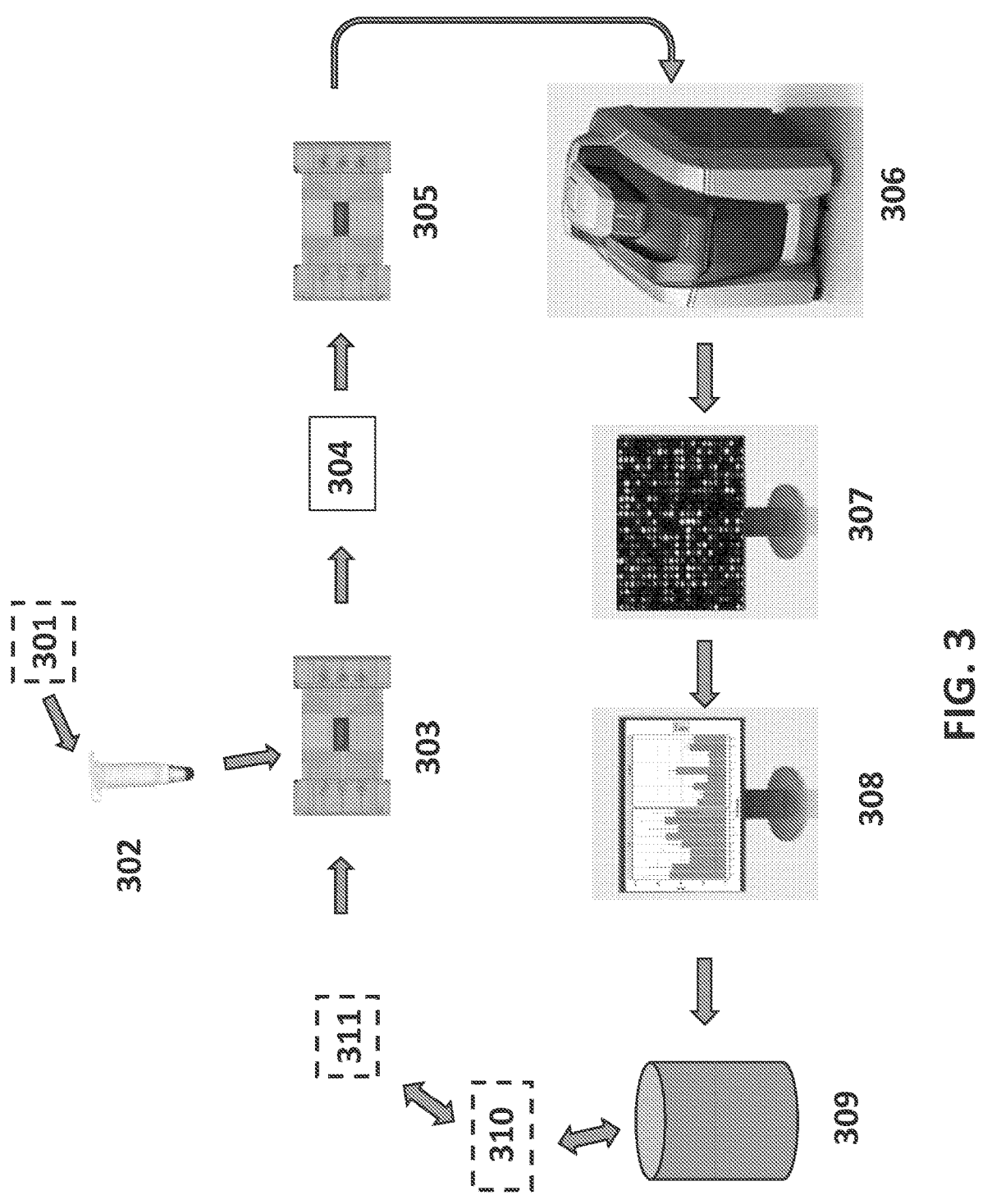
FIG. 3 shows an exemplary workflow employing independent sample sections.

An example workflow is outlined in FIG. 3. A patient sample 301 (e.g., blood, bacterial swab) is collected and sample nucleic acids are labeled 302. The labeled sample is loaded into a flow cell 303 comprising an independent sample section "chiplet" on which probes are loaded, for example as a bead array. In an example, the probes are for targets to identify infectious diseases, bacteria, viruses, and antimicrobial resistance traits. Isotachophoresis (ITP) 304 is used to contact the labeled sample nucleic acids to the chiplet and the sample is allowed to hybridize to the chiplet for 30 minutes. After hybridization, unhybridized sample nucleic acids are washed 305 from the chiplet without the chiplet being removed from the flow cell. The flow cell with the chiplet is read optically 306 (e.g., in a fluorescence chip reader such as from Keyence) to detect binding of labeled sample nucleic acids. The fluorescent images are scanned and analyzed 307 to determine the presence of labeled sample nucleic acids bound to probes on the chiplet. Based on the identity of the probes located on the beads to which sample nucleic acids have bound, the presence of certain targets (e.g., pathogens and infectious agents, microorganisms, traits such as resistance or pathogenicity) can be determined and presented in a report 308.

Information from individual chiplet assays can be used to improve 309 the analysis of subsequent samples. For example, machine learning approaches 310 can be used to refine analysis and/or the design of future probe sets 311.

What is claimed is:

1. A method comprising:
a) obtaining an array substrate comprising a plurality of sections, wherein each section of the plurality of sections comprises:
a plurality of array sites, wherein the plurality of array sites comprises a plurality of probes,
wherein a target or sequence of the plurality of probes at the plurality of array sites have been previously determined,
wherein each section of the plurality of sections are set apart from other sections of the plurality of sections by buffer zones, wherein a width of the buffer zones is less than or equal to about 100 micrometers (μm);
b) determining:
(i) identities of targets that bind to the plurality of probes at the plurality of array sites, and/or (ii) sequences of the plurality of probes at the plurality of array sites;
c) generating a plurality of chiplets by physically separating the array substrate in to multiple separated components, wherein each chiplet of the plurality of chiplets comprises a section of the plurality of sections; and
d) determining targets or sequences of probes of a chiplet of the plurality of chiplets, based at least on identifying the chiplet as corresponding to a particular section of the plurality of sections.

2. The method of claim 1, wherein the array substrate is a bead array substrate and wherein the plurality of array sites comprise beads in wells, wherein the beads comprise the plurality of probes.

3. The method of claim 1, wherein the chiplet further comprises one or more fiducials and wherein the determining targets or sequences of probes of a chiplet of the plurality of chiplets comprises observing the presence of the one or more fiducials on the chiplet of the plurality of chiplets.

4. The method of claim 1, wherein the determining targets or sequences of probes of a chiplet of the plurality of chiplets comprises physically labeling at least some of the plurality of array sites.

5. The method of claim 4, wherein the labeling comprises labeling array sites of the plurality of array sites that do not contain probes.

6. The method of claim 1, wherein the determining targets or sequences of probes of a chiplet of the plurality of chiplets comprises parsing a decoding file into subfiles for each section of the plurality of sections.

7. The method of claim 1, wherein the plurality of probes comprise oligonucleotides or proteins.

8. The method of claim 1, wherein the physically separating the array substrate in to multiple components comprises dicing, etching, or cutting the array substrate.

9. The method of claim 1, wherein a section of the plurality of sections comprises fewer than 10,000,000 array sites.

10. The method of claim 1, wherein a section of the plurality of sections comprises fewer than 1,000,000 array sites.

11. The method of claim 1, wherein a section of the plurality of sections comprises fewer than 100,000 array sites.

12. The method of claim 1, wherein a section of the plurality of sections comprises fewer than 10,000 probes per array site.

13. The method of claim 1, wherein a section of the plurality of sections comprises fewer than 5,000 probes per array site.

14. The method of claim 1, wherein a section of the plurality of sections comprises fewer than 1,000 probes per array site.

15. The method of claim 1, wherein an array site of the plurality of array sites comprises fewer than 10,000 probes.

16. The method of claim 1, wherein an array site of the plurality of array sites comprises fewer than 1,000 probes.

17. The method of claim 1, wherein the width of the buffer zones is less than or equal to 50 micrometers (μm).

* * * * *